United States Patent [19]

Meade

[11] Patent Number: 5,631,031
[45] Date of Patent: May 20, 1997

[54] WATER-INSOLUBLE AMINO ACID SALT

[76] Inventor: Thomas L. Meade, 187 Walmsley La., Saunderstown, R.I. 02874

[21] Appl. No.: 260,450

[22] Filed: Jun. 13, 1994

[51] Int. Cl.⁶ .............................. A23K 1/16; A23K 1/18; A23K 1/22; A23L 1/305
[52] U.S. Cl. .............. 426/2; 426/549; 426/656; 426/807; 426/648; 562/560; 562/562; 562/570; 562/575; 562/559; 562/443; 548/344; 548/339.1
[58] Field of Search ................ 426/2, 656, 807, 426/648; 562/562, 570, 575, 559, 443, 560; 548/344, 496

[56]  References Cited

U.S. PATENT DOCUMENTS

| | | |
|---|---|---|
| 2,833,821 | 5/1958 | Hause . |
| 3,015,567 | 1/1962 | Hause et al. . |
| 3,617,297 | 11/1971 | Sawaki et al. . |
| 3,976,680 | 8/1976 | Clark et al. .............. 260/471 |
| 4,000,318 | 12/1976 | Ferguson et al. .............. 426/2 |
| 4,021,569 | 5/1977 | Abdel-Monem . |
| 4,067,994 | 1/1978 | Anderson et al. . |
| 4,073,945 | 2/1978 | Bertram et al. . |
| 4,076,745 | 2/1978 | Lodewyk . |
| 4,172,072 | 10/1979 | Ashmead . |
| 4,425,280 | 1/1984 | Ho . |
| 4,446,055 | 5/1984 | Shah et al. . |
| 4,664,905 | 5/1987 | Meyer . |
| 4,764,633 | 8/1988 | Anderson et al. . |
| 4,830,716 | 5/1989 | Ashmead . |
| 4,996,067 | 2/1991 | Kobayashi et al. . |
| 5,216,021 | 6/1993 | Sorenson . |
| 5,278,329 | 1/1994 | Anderson . |
| 5,292,538 | 3/1994 | Paul et al. . |

OTHER PUBLICATIONS

Myer Food Chemistry, 1960, Reinold Publishing Corp. New York. p. 122.

Primary Examiner—Esther Kepplinger
Assistant Examiner—Choon P. Koh
Attorney, Agent, or Firm—Rothwell, Figg, Ernst & Kurz

[57]  ABSTRACT

Disclosed are water-insoluble, calcium or magnesium salts of alpha amino acids and a process for their preparation. The process comprises the steps of reacting an alpha-amino-protected alkyl ester of an amino acid with a metal base, thereby forming a water-soluble amino acid salt, followed by reacting the water-soluble salt with either a calcium or magnesium salt, resulting in the formation of a water-insoluble salt of the amino acid. The water-insoluble salts can be used as feed supplements for ruminant animals and to supplement food products for human consumption.

30 Claims, No Drawings

WATER-INSOLUBLE AMINO ACID SALT

FIELD OF THE INVENTION

The present invention relates to the preparation of water-insoluble salts of alpha amino acids, to these salts per se, and to the use of such water-insoluble salts of alpha amino acids for improving the nutritive value of animal feed and food products for human consumption. More particularly, the invention relates to water-insoluble salts of alpha amino acids that are insoluble under conditions within certain portions of the digestive system of a feed animal, yet are soluble under conditions within other portions of the animal's digestive system.

BACKGROUND OF THE INVENTION

Amino acids are the basic components of proteins in both food for human consumption and animal feed. Amino acids are classified as either "essential" or "non-essential." The amino acid composition of proteins is varied and distinct for each protein. Proteins having a vegetable or microbial origin usually lack an ideal balance of the essential amino acids required by higher forms of animal life including humans. In order to correct for any deficiencies in the amino acid content of vegetable proteins, proteins of animal origin are often fed in conjunction with vegetable proteins. Attempts have also been made to correct any amino acid deficiency by supplementing both human food and animal feed with the specific amino acids that are limiting.

Supplementing livestock and poultry feeds with amino acids is a well-established and widely accepted practice. For example, lysine monohydrochloride, dl-methionine and methionine hydroxy analog are amino acid supplements used in large volume in the feed industry.

It is also well established to supplement animal feed with amino acids complexed with a variety of metals, including calcium and various transition metals, including copper, zinc and iron. The purpose of these metal-amino acid complexes is to supply dietary requirements of both metal ions and essential amino acids to the animal. However, so that the metal-amino acid complexes can be provided in an effective bioavailable form, the complexes are described in the art as water-soluble, which allows the metal and/or amino acid to be readily absorbed after ingestion.

A series of patents assigned to Zinpro Corporation relates to water-soluble "complex salts" of transition metals and alpha amino acids, in particular for use as feed additives and animal nutrition. For example, U.S. Pat. No. 4,021,569, issued to M. Abdel-Monem on May 3, 1977 relates to 1:1 zinc methionine complex salts. The patent describes the complex salts as containing a coordination bond formed between the zinc and the alpha-amino group, in addition to an electrostatic attraction bond between the zinc and the carboxylic acid group. The 1:1 complex salts of zinc and methionine are reported to be of great importance in ensuring absorption of the zinc and methionine and their subsequent distribution and effective utilization in animals. Because the 1:1 complex salts are water-soluble, the zinc and methionine are disclosed as being readily utilized after ingestion.

Other Zinpro patents relating to water soluble complexes of metal ions and amino acids include U.S. Pat. Nos. 4,948,594, 4,900,561, 4039,681, 4,067,994, 4,764,633 and 5,278,329.

U.S. Pat. No. 5,278,329 teaches that the complexes which are the subject matter of the above listed Zinpro patents are characterized as 1:1 complex salts because 1:1 complex salts are more water-soluble, more bioavailable and more efficiently converted to provide the maximum effective body usage of both the transition metal and the amino acid.

While the processes of fermentation and digestion which take place in the rumen of ruminant animals largely benefit the animals under natural feeding conditions, modern husbandry requires that, for optimum production of meats and/or milk, ruminant animals should be fed a proportion of their dietary requirements in the form of nutrients which will not undergo any alteration or degradation in the rumen. It also is necessary, however, that such nutrients not interfere with the normal processes of rumen fermentation.

Proteins used in ruminant feeds are largely of vegetable origin and thus may be supplemented with sources of non-protein nitrogen to help support the growth of microorganisms in the rumen. The primary source of protein for post-ruminal digestion and absorption is rumen microbial protein. In the case of protein metabolism, however, it is known that at certain periods during the growth, development and lactation of cows, insufficient microbial protein is produced in the rumen to meet the animal's full requirements for maximum growth or maximum milk production. It is therefore desirable that a proportion of the protein requirement of cows be met by supplying a supplement containing protein or individual essential amino acids which are not degraded in the rumen. This can improve feed conversion efficiency, growth rate and production as compared with using an equal weight of degradable protein or amino acid.

There have been a number of methods proposed for protecting fats and proteins from the effects of rumen fermentation so that they are not digested until they reach the abomasum or intestine of the ruminant. These methods have for the most part depended upon protecting such fats and/or proteins (and sometimes other nutritional materials such as minerals or essential vitamins) via a coating which resists the fermentation processes of the rumen.

There exists a need for being able to feed to a ruminant animal essential amino acids in a form in which the degradative effects of the normal fermentation and digestion processes in the rumen can be minimized or avoided. More specifically, a need exists for a form of amino acid that can bypass normal fermentation and digestion processes of the rumen and reach the abomasum or intestine of the ruminant in a form in which the animal can take the fullest advantage of the nutritive value of the amino acid.

Although amino acids are available from pharmacies, health food stores and supermarkets, their value as food supplements for humans is uncertain in most cases. The most widely used amino-acid-based supplement is monosodium glutamate, which functions as a flavor enhancer.

The sale of pasta products world-wide occupies a very large volume market. In the United States and many other countries, these products contain a very high percentage of processed semolina wheat. During the course of preparing this ingredient, the quality of the protein is degraded, thus causing a deficiency in the lysine content of the protein. Furthermore, the manner in which pasta is prepared for consumption, namely boiling in water, largely precludes any value of supplementing pasta products with lysine because the lysine can easily leach out of the pasta during boiling. Thus, there also exists a need for an additive for food products for human consumption, specifically pasta, containing one or more essential amino acids in a form such that when the additive is combined with a food product, the amino acid remains in the food product after boiling or other means of cooking.

One objective of the present invention is therefore to provide a process for preparing a water-insoluble, calcium or magnesium salt of an alpha amino acid.

Another important objective of the present invention is to provide a feed supplement for ruminant animals comprising a water-insoluble salt of an alpha amino acid, which is able after ingestion to bypass the normal fermentation and digestion processes which occur in the rumen of a ruminant animal.

A further objective of the present invention is to provide an enriched food product for human consumption which contains a water-insoluble salt of an alpha amino acid which allows the food product to maintain substantially all of the amino acid during and after normal manufacturing and cooking processes.

The method of accomplishing these and other objectives will become apparent in the following description of the invention.

SUMMARY OF THE INVENTION

In one aspect, the present invention is directed to a water-insoluble amino acid salt having the formula:

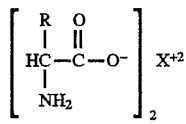

wherein:

X is calcium or magnesium, and

R is the R group of any of the twenty naturally occurring (or "standard") amino acids, and ornithine.

Another aspect of the present invention provides a feed supplement for ruminant animals comprising a water-insoluble amino acid salt of the above formula. The solubility characteristics of the amino acid salt allow it to bypass the normal fermentation and digestion processes which occur after ingestion in the rumen of a ruminant animal. The ingested amino acid can bypass the rumen and reach the abomasum or intestine of the ruminant, thus permitting the ruminant to take the fullest advantage of the nutritive value of the amino acid. In the case of lactating dairy cattle, the increased nutritive value provided by the water-insoluble salt of the amino acid helps to enhance milk production, whereas in the case of beef cattle, it helps to enhance meat production.

A further aspect of the present invention is directed to an enriched food product for human consumption which comprises flour, or some other food-compatible carrier, and a water-insoluble amino acid salt of the above formula. When the insoluble amino acid salts are combined with a food product, the food product can maintain the amino acid during and after normal manufacturing and cooking processes.

The present invention is also directed to a method for enhancing the nutrition and health of a ruminant animal by feeding to the ruminant a water-insoluble amino acid salt of the above formula.

Another aspect of the present invention is a method for enhancing the nutritive value of a food product for human consumption by adding to the food product during its manufacture a water-insoluble amino acid salt of the above formula.

The present invention is further directed to a process for preparing water-insoluble amino acid salts by reacting an alpha-amino-protected ester of an alpha amino acid with a metal base to form a water-soluble metal salt. The water-soluble metal salt is then reacted with either a calcium or magnesium salt, whereupon a water-insoluble amino acid salt is formed. The insoluble salt is easily recovered from the reaction solution.

These and other features, aspects and advantages of the present invention will become better understood with reference to the following description and appended claims.

DETAILED DESCRIPTION OF THE INVENTION

The compounds of the present invention can be described as water-insoluble, bivalent salts of alpha amino acids having the general formula:

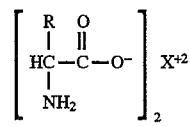

wherein:

X is calcium or magnesium, and

R is the R group of any of the twenty naturally occurring (or "standard") amino acids, and ornithine (See A. L. Lehninger, *Biochemistry*, pgs. 72–77 (2nd Edition)).

The term "water-insoluble" defines an amino acid salt which is substantially insoluble in water at about pH 5.5 or higher and is substantially soluble at about pH 3.0 or lower. "Water-insoluble" also means that the amino acid salt remains substantially insoluble in the rumen of a ruminant animal, thus ensuring that a major proportion fed to the animal passes through the rumen, while being substantially soluble and therefore assimilable under the relatively lower pH conditions of the post-rumen digestive system, in particular within the abomasum and small intestine, of the ruminant animal.

It is important to note that the salts of the present invention are formed as a result of an ionic bond between either a calcium or magnesium cation and the carboxyl ion of the amino acid. Unlike water-soluble metal-amino acid complexes in the prior art, in which a coordination bond is formed between a metal cation and the alpha amino group of the amino acid in addition to the electrostatic attraction between the cation and the carboxyl ion, the salts of the present invention lack a coordination bond between the metal cation and the alpha amino group.

Although the salts of the present invention can be prepared by employing any alpha amino acid, the preferred alpha amino acids are the "essential" alpha amino acids arginine, histidine, isoleucine, leucine, lysine, methionine, phenylalanine, threonine, tryptophan, and valine. Another preferred alpha amino acid, while not "essential," is ornithine. The water-insoluble calcium and magnesium salts of lysine, methionine and ornithine are particularly preferred.

The preferred calcium-L-lysinate and calcium-L-methionate salts prepared according to the process of the present invention have the general formula:

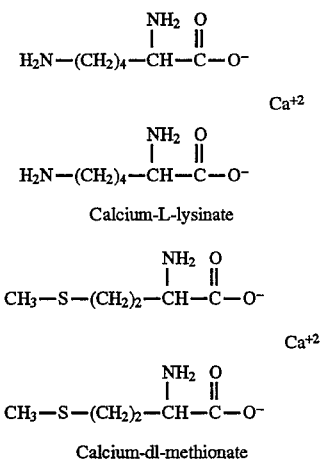

Calcium-L-lysinate

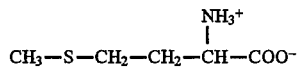

Calcium-dl-methionate

Other preferred compounds according to the present invention are magnesium-L-lysinate, magnesium-dl-methionate, calcium-L-ornithate and magnesium-L-ornithate.

As mentioned above, a preferred essential alpha amino acid for preparing the salts of the present invention is methionine. The structure for dl-methionine in solution is reproduced below:

$$CH_3-S-CH_2-CH_2-\underset{\underset{NH_3^+}{|}}{CH}-COO^-$$

The amino and carboxyl groups are shown in their ionized form. This form is commonly referred to as a zwitterion, within which the positive amino group and negative carboxyl group are equally ionized, thus causing the alpha amino acid molecule to have a net charge of zero in solution. As known in the art, different amino acids possess a net charge of zero in solution at different pH levels. This particular pH level is commonly referred to as the isoelectric point of the amino acid.

The ionized carboxyl group of the free amino acid is unable to react with a weak base such as calcium hydroxide ($Ca(OH)_2$), or even a strong base such as sodium hydroxide (NaOH), unless the alpha amino group of the amino acid molecule is somehow protected or blocked from reacting with the base, and the hydrogen ion missing from the ionized carboxyl group is restored. An "alpha-amino-protected alkyl ester," which is a preferred starting material for preparing the salts of the present invention, is thus defined as an alkyl ester of an alpha amino acid on which the alpha amino group is blocked or protected by a chemical group, including for example, a hydrochloride ion. Other protecting or blocking groups for the alpha amino group can be used.

The preferred process for preparing the water-insoluble amino acid salts of the present invention begins with the use of any alpha-amino-protected, straight or branched alkyl ester of an alpha amino acid. Methyl, ethyl and higher molecular weight straight-chain and branched alkyl esters of amino acid monohydrochlorides and dihydrochlorides, which are commercially available, are preferably used. These esters can be produced according to the following reaction sequence. For example, when reacting lysine monohydrochloride, a commercial product widely used in the feed industry, with hydrochloric acid and methanol, the reaction will proceed as follows:

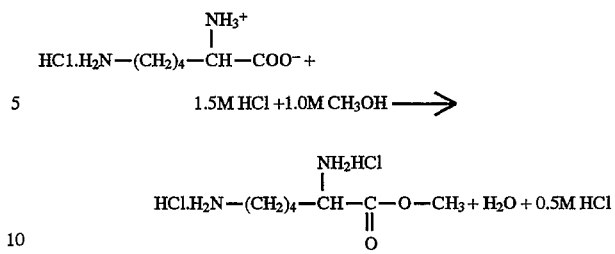

One of skill in the art will recognize that other acids could be used in place of the preferred hydrochloric acid to neutralize and form the protecting group on the alpha amino group of the lysine molecule. Additionally, other alcohols could be used in place of the preferred methanol to form other corresponding straight-chain or branched alkyl esters of the alpha amino acid, including ethanol and butanol.

The above reaction preferably is carried out under reflux conditions at a temperature of about 78° C. to about 82° C. for about 30 minutes to about 1 hour in the presence of an excess amount of methanol, preferably 3 to 5 moles, to facilitate the dissolution of the lysine monohydrochloride. The hydrochloric acid can be introduced in the form of a gas which condenses in the methanol-lysine hydrochloride solution.

The product obtained from the above reaction, methyl-L-lysine dihydrochloride ester, exists in the liquid state at the distillation temperatures of the reaction. Thus, any excess methanol, water and hydrochloric acid can be removed from the reaction solution by conventional methods.

The methyl-L-lysine dihydrochloride ester in its ionized form is converted to one of the preferred water-insoluble amino acid salts of the present invention by first converting the methyl ester to a water soluble salt, in accordance with the following reaction sequence:

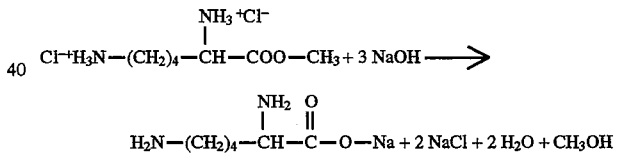

Other metal bases can be used in place of sodium hydroxide to form the water-soluble salt.

The above reaction is highly exothermic and must be carried out with appropriate safeguards. The production of sodium chloride (NaCl) exceeds its solubility and thus precipitates out of the reaction solution. It is desireable that the temperature of the reaction be maintained in the range of about 50° C. to about 100° C., and preferably of about 65° C. to about 70° C., to minimize the evaporation of any released methanol. The reaction is carried out for about 20 to about 60 minutes, and preferably about 30 minutes.

Once the above reaction is completed, the reaction products are heated (for example, to a temperature between about 90° C.–110° C., more preferably about 103° C.–105° C.) to drive off any remaining methanol and to insure that the ester is substantially converted to the sodium salt of lysine, sodium lysinate.

As mentioned above, the sodium lysinate is water-soluble and is converted to the water-insoluble, divalent ion salt of lysine. This final reaction can be carried out to produce either calcium-L-lysinate or magnesium-L-lysinate.

The reaction solution, still under basic conditions, is heated to about 90° C. to about 110° C., more preferably about 103° C. to about 105° C. Enough water is added to resolubilize the precipitated sodium chloride.

The aqueous solution of sodium lysinate and sodium chloride is then reacted with a saturated solution of calcium chloride, for forming calcium-L-lysinate, or magnesium chloride, for forming magnesium-L-lysinate, at a temperature of about 50° C. to about 80° C., preferably of about 55° C. to about 60° C., for a period of about 20 to about 60 minutes, and preferably about 30 minutes, in accordance with the following reaction sequence:

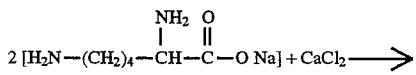

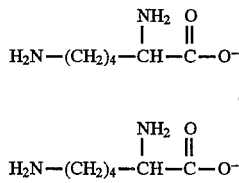

Other sources of calcium and magnesium ions can be used.

The calcium-L-lysinate forms rapidly during the above reaction and, as mentioned above, is insoluble under the reaction conditions. It thus can be removed from the aqueous sodium chloride solution by any conventional separation process, including filtration or centrifugation. Washing the recovered calcium-L-lysinate one or more times will remove any residual sodium chloride and produce a product having high purity.

The calcium-L-lysinate can be dehydrated by most, if not any, established dehydration procedures.

In order to illustrate the versatility of the present invention, the process will next be described using dl-methionine, in accordance with the following reaction sequence:

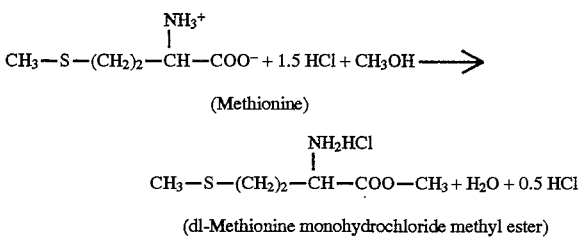

The product of the above reaction, the methyl ester hydrochloride of methionine, can be reacted with 2.5 moles of NaOH to form a water soluble sodium salt of methionine along with producing selected byroducts, as shown below:

The water-soluble sodium salt then can be converted to a water-insoluble calcium salt, calcium-dl-methionate, as shown by the following reaction sequence:

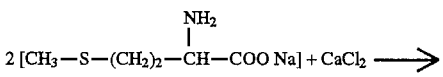

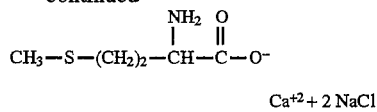

(Calcium dl-methionate)

The process of the present invention also can be used to prepare a water-insoluble salt of ornithine. The reaction can proceed in accordance with the following reaction sequence:

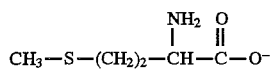

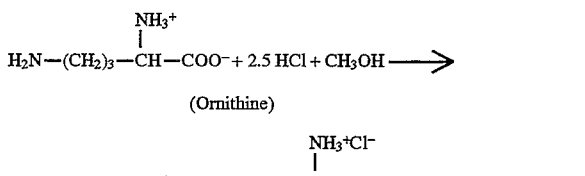

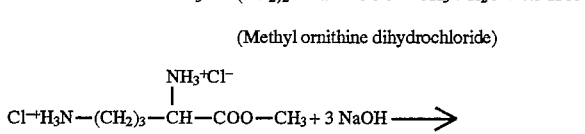

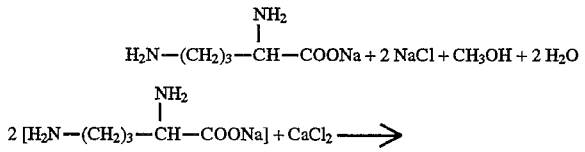

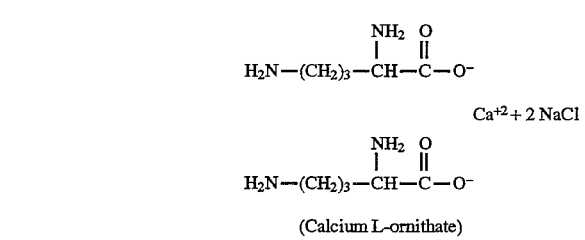

(Calcium L-ornithate)

The previously described salts of the present invention have many advantages, including that they are stable, water-insoluble in desired pH ranges and can be easily and relatively inexpensively produced in large quantities for use as food additives for human consumption and as feed supplements for ruminant animals.

To achieve the optimum production of meat and/or milk in ruminant animals, the ruminants can be fed a proportion of their dietary requirements by using the water-insoluble salts of the present invention. An important advantage of the water-insoluble salts of the present invention is that they will not undergo undesirable alteration or degradation in the rumen after ingestion, and thus will not be available to the microorganisms of the rumen. In addition, the water-insoluble salts of the present invention will not interfere with the normal processes of rumen fermentation. The advantage improves feed conversion efficiency, growth rate and production as compared with using equal weight of a degradable protein or amino acid.

The insolubility of the amino acid salts of the present invention allows the amino acid salt to bypass the normal fermentation and digestion processes of the ruminant animal and reach the abomasum or intestine of the ruminant in a form in which it can be absorbed. This feature allows the ruminant to take the full advantage of the nutritive value of the amino acid.

Another distinct advantage of the water-insoluble amino acid salts of the present invention is their use in food products for human consumption. For example, when the water-insoluble amino acid salts are added to food products, in particular pasta, the salts are able to remain in the food product after boiling or other means of cooking. In general, enriched food products containing one or more of the water-insoluble amino acid salts can be prepared by mixing the salt with any type of flour, including wheat, oat or corn flour, or some other food compatible carrier, and water. In particular, food products in which corn (Zea mays) is the primary ingredient will be improved by combining the food product with the water-insoluble salts of the present invention.

The level of addition of the water-insoluble amino acid salts for use a feed supplement can vary over a wide range and will be selected based on known nutritional requirements. For example, satisfactory levels are achieved when the amount of the preferred water-insoluble amino acid salt of calcium-L-lysinate, calcium-dl-methionate, and calcium-L-ornithate, as well as others, added to animal feed, is from about 20 grams per head of cattle a day to about 50 grams per head of cattle per day. It should, however, be understood that other levels of addition can be utilized and that the precise level of addition will be selected according to well known nutritional criteria.

Nutritional supplements for addition to the diets of ruminant animals are prepared by combining one or more water-insoluble amino acid salts of the present invention with a ruminant-feed-compatible carrier or filler material. Examples of suitable carriers include edible particulate materials including feed grains, animal byproducts and pelletized celluosic materials. The water-insoluble amino acid salts of the present invention will provide the ruminant animal with appropriate levels of the essential amino acids to provide normal healthy growth, as well as enhance meat production in beef cattle and milk production in lactating dairy cattle.

The following examples are offered to illustrate, but not limit, the preparation of compounds and compositions according to the present invention.

EXAMPLE 1

Preparation of a Water-Insoluble Calcium Salt of Lysine

The reaction for preparing the water-insoluble calcium salt of lysine is carried out in a 5 liter round bottom flask surrounded by an ice water bath. The flask is equipped for agitation, addition and condensation.

Two moles (64 grams) of methanol are added, followed by the addition of one mole (233.1 grams) of methyl L-lysine monohydrochloride. The reaction mixture is stirred for 5 minutes to insure that the solute is solubilized. Three moles (120 grams) of sodium hydroxide in a concentrated aqueous solution are added under agitation to neutralize the L-lysine dihydrochloride. The reaction is run for 30 minutes in a temperature range of 55°–60° C. to minimize the evaporation of methanol from the reaction mixture. Upon completion of the above reaction, the methyl ester of L-lysine is converted to the sodium salt of L-lysine.

Enough water is added to solubilize any precipitated sodium chloride.

One half mole (55.5 grams) of calcium chloride in a saturated aqueous solution is added to the reaction mixture containing the sodium salt of L-lysine. The calcium chloride is reacted with the sodium salt of L-lysine for 30 minutes at a temperature of 55°–60° C. The calcium salt of L-lysine is formed as a precipitate which can be separated from the reaction mixture by either filtration or centrifugation.

The filtrate or precipitate is rinsed with water to reduce any residual sodium chloride that is present.

The recovered calcium salt of L-lysine is dehydrated by conventional methods.

EXAMPLE 2

Preparation of a Magnesium Salt of Lysine

The process described in Example 1 is carried out, except that one half mole (47.6 grams) of magnesium chloride is added in a saturated aqueous solution in place of calcium chloride. A precipitate of the magnesium salt is formed which is thereafter removed by conventional methods, such as filtration or centrifugation.

EXAMPLE 3

The reaction conditions of Example 1 are repeated, except that the starting material is the already-prepared methyl ester of L-lysine dihydrochloride. Water is therefore used as a solvent in place of methanol.

The reaction is carried out in a 5 liter round bottom flask surrounded by an ice water bath. The flask is equipped for agitation, addition, and condensation.

250 ml of water are added to the flask, followed by the one mole (233.1 grams) of methyl L-lysine dihydrochloride. The reaction mixture is stirred for 5 minutes to insure that any solute is dissolved.

Three moles (120 grams) of sodium hydroxide in a concentrated aqueous solution are added under agitation to neutralize the L-lysine dihydrochloride. The reaction is carried out for 30 minutes while the temperature is maintained at 65°–70° C. to minimize any evaporation of methanol. Upon completion of the above reaction, the methyl ester of L-lysine is converted to the sodium salt of L-lysine. Enough water is added to fully dissolve any sodium chloride products not already solubilized in the reaction mixture.

The product from the above reaction is then reacted with calcium chloride or magnesium chloride, under the reaction conditions of Examples 1 and 2, respectively.

EXAMPLE 4

Preparation of Calcium or Magnesium Salts of Methionine

A similar process as used in Examples 1 and 2 is carried out, except that 2 moles (80 grams), rather than 3, of sodium hydroxide in a concentrated aqueous solution are used to neutralize the methyl ester of DL-methionine monohydrochloride and cause the formation of the water-soluble, DL-methionine sodium salt.

EXAMPLE 5

Preparation of Enriched Pasta

The water-insoluble calcium or magnesium salts of lysine prepared according to Examples 1 and 2, respectively, are mixed with semolina flour. This enriched flour is used as an ingredient in the preparation of a dough which is processed according to procedures known in the art to produce a pasta product.

Although the invention has been described in connection with certain preferred embodiments, it is not so limited.

Alterations and variations within the spirit and scope of the claims will be apparent to those skilled in the art.

What is claimed is:

1. A water-insoluble amino acid salt of the formula:

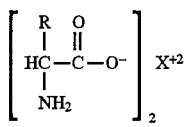

wherein:

X is calcium or magnesium, and

R is the R group of any of the twenty naturally occurring amino acids, and ornithine.

2. A water-insoluble amino acid salt according to claim 1, wherein the amino acid salt is substantially insoluble in water at about pH 5.5 or higher and substantially soluble at about pH 3.0 or lower.

3. A water-insoluble amino acid salt according to claim 1, wherein the amino acid salt substantially does not solubilize or metabolize in the rumen of a ruminant animal, while being substantially soluble and therefore assimilable and metabolizable under the low pH conditions of the post-rumen digestive system of the ruminant animal.

4. A feed supplement for ruminant animals, comprising a water-insoluble amino acid salt according to claim 1 and a ruminant-feed-compatible carrier.

5. A feed supplement for ruminant animals, according to claim 4, wherein R is the R group of any of the essential amino acids selected from the group consisting of histidine, isoleucine, leucine, lysine, methionine, phenylalanine, threonine, tryptophan, valine, and arginine.

6. A feed supplement for ruminant animals according to claim 5, wherein the essential amino acid is lysine.

7. A feed supplement for ruminant animals according to claim 5, wherein the essential amino acid is methionine.

8. A feed supplement for ruminant animals according to claim 4, wherein R is the R group of ornithine.

9. An enriched food product comprising a water-insoluble amino acid salt according to claim 1 and flour.

10. An enriched food product according to claim 9, wherein the food product is pasta.

11. An enriched food product according to claim 9, wherein R is the R group of any of the essential amino acids selected from the group consisting of histidine, isoleucine, leucine, lysine, methionine, phenylalanine, threonine, tryptophan, valine, and arginine.

12. An enriched food product according to claim 11, wherein the essential amino acid is lysine.

13. An enriched food product according to claim 11, wherein the essential amino acid is methionine.

14. A method for enhancing the nutrition and health of a ruminant, comprising the step of feeding to the ruminant a water-insoluble amino acid salt according to claim 1.

15. A method according to claim 14, wherein R is the R group of any of the essential amino acids selected from the group consisting of histidine, isoleucine, leucine, lysine, methionine, phenylalanine, threonine, tryptophan, valine and arginine.

16. A method according to claim 15, wherein the essential amino acid is lysine.

17. A method according to claim 15, wherein the essential amino acid is methionine.

18. A method according to claim 15, wherein R is the R group of ornithine.

19. A process for preparing a water-insoluble salt of an alpha amino acid, which comprises the steps of:

a) reacting an alpha-amino-protected alkyl ester of the amino acid with a metal base to form a water soluble metal salt; and b) reacting the water soluble metal salt with a water soluble metal salt selected from the group consisting of a calcium salt and a magnesium salt.

20. A process according to claim 19, wherein the alkyl ester is a straight or branched chain alkyl ester.

21. A process according to claim 20, wherein the alkyl ester of the amino acid is a methyl ester.

22. A process according to claim 21, wherein the methyl ester is selected from the group consisting of methyl-amino acid monohydrochloride and methyl-amino acid dihydrochloride.

23. A process according to claim 19, wherein the amino acid is an essential amino acid selected from the group consisting of histidine, isoleucine, leucine, lysine, methionine, phenylalanine, threonine, tryptophan, valine and arginine.

24. A process according to claim 23, wherein the essential amino acid is lysine.

25. A process according to claim 23, wherein the essential amino acid is methionine.

26. A process according to claim 19, wherein the alpha amino acid is ornithine.

27. A process according to claim 19, wherein the metal base is sodium hydroxide.

28. A water-insoluble salt of an alpha amino acid, made according to the process of claim 19.

29. A food supplement for ruminants, comprising a ruminant-feed-compatible carrier and a water-insoluble salt of an alpha amino acid, made according to the process of claim 19.

30. An enriched food product, comprising flour and a water-insoluble salt of an alpha amino acid, made according to the process of claim 19.

* * * * *